United States Patent
Auvray et al.

(10) Patent No.: US 11,992,276 B2
(45) Date of Patent: May 28, 2024

(54) PERSISTENT GUIDE WIRE IDENTIFICATION

(71) Applicant: KONINKLIJKE PHILIPS N.V., Eindhoven (NL)

(72) Inventors: Vincent Maurice André Auvray, Meudon (FR); Raoul Florent, Ville d'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 320 days.

(21) Appl. No.: 17/442,098

(22) PCT Filed: Mar. 25, 2020

(86) PCT No.: PCT/EP2020/058383
§ 371 (c)(1),
(2) Date: Sep. 22, 2021

(87) PCT Pub. No.: WO2020/193640
PCT Pub. Date: Oct. 1, 2020

(65) Prior Publication Data
US 2022/0160432 A1    May 26, 2022

(30) Foreign Application Priority Data
Mar. 26, 2019  (EP) .................................... 19290019

(51) Int. Cl.
*A61B 34/20* (2016.01)
*A61B 6/12* (2006.01)
(Continued)

(52) U.S. Cl.
CPC ................ *A61B 34/20* (2016.02); *A61B 6/12* (2013.01); *A61B 6/463* (2013.01); *G16H 30/40* (2018.01); *A61B 2034/2051* (2016.02)

(58) Field of Classification Search
CPC ........... A61B 34/20; A61B 6/12; A61B 6/463; G16H 30/40
See application file for complete search history.

(56) References Cited

U.S. PATENT DOCUMENTS 8,255,037 B2    8/2012  Florent
2010/0121181 A1   5/2010  Wang
(Continued)

FOREIGN PATENT DOCUMENTS

WO    2016134980 A1    9/2016

OTHER PUBLICATIONS

International Search Report and Written Opinion of PCT/EP2020/058383, dated Jun. 18, 2020.
(Continued)

*Primary Examiner* — Gerald Johnson

(57) ABSTRACT

A system (IPS) for supporting image-based navigation, comprising: an input interface (IN) for reviving one or more input images acquired by an X-ray imager (IA) whilst two or more medical devices (GW1, GW2) are present in a field of view (FoV) of the X-ray imaging apparatus. An image identifier (ID) identifies the two or more medical devices based on image information in the one or more images. A tagger (TGG) associates a respective, unique, tag with each of at least two of the two or more medical devices (GW1, GW2) so identified. A graphics display generator (GDG) effects displaying on a display device (DD) the one or more input images in a video feed, with the tags included.

13 Claims, 6 Drawing Sheets

(51) Int. Cl.
*A61B 6/46* (2024.01)
*G16H 30/40* (2018.01)

(56) References Cited

U.S. PATENT DOCUMENTS

| | | |
|---|---|---|
| 2012/0271162 A1 | 10/2012 | Liao |
| 2015/0005620 A1 | 1/2015 | Bergman |
| 2017/0024910 A1 | 1/2017 | Griffin |
| 2018/0235509 A1 | 8/2018 | Doron |
| 2019/0213741 A1* | 7/2019 | Nagae ................. G06T 7/246 |

OTHER PUBLICATIONS

Zheng, Y. et al "Marginal Space Learning for Efficient Detection of 2D/3D Anatomical Structures in Medical Images", Inf. Process Med. Imaging, vol. 21, pp. 411-422, 2009.

Vandini, Alessandro et al "Robust Guidewire Tracking under Large Deformations Combining Segment-Like Features (SEGlets)", Medical Image Analysis, vol. 38, pp. 150-14, 2017.

Wagner, Martin G. et al "Guidewire Path Tracking and Segmentation in 2D Fluoroscopic Time Series using Device Paths from Previous Frames", Proceedings of SPIE Medical Imaging, vol. 9784, 2016.

Wang, Peng et al "Hierarchical guidewire tracking in fluoroscopic sequences", Medical Imaging: Image Processing, 2009.

Wang, Peng et al "Robust guidewire tracking in fluoroscopy", CVPR 2009: pp. 691-698.

* cited by examiner

PERSISTENT GUIDE WIRE IDENTIFICATION

CROSS-REFERENCE TO PRIOR APPLICATIONS

This application is the U.S. National Phase application under 35 U.S.C. § 371 of International Application No. PCT/EP2020/058383, filed on Mar. 25, 2020, which claims the benefit of European Patent Application No. 19290019.9, filed on Mar. 26, 2019. These applications are hereby incorporated by reference herein.

FIELD OF THE INVENTION

The invention relates to a system for supporting image-based navigation, to a method for supporting image-based navigation, to a computer program element, and to a computer-readable medium.

BACKGROUND OF THE INVENTION

In certain medical interventions, such as percutaneous coronary intervention (PCI), a clinician sometimes needs to introduce into the patient several (e.g., three or more) medical devices or tools, such as guide wires. For example, the clinician may start treating a stenosis in one branch of the coronaries, and then switch to another branch where a bifurcation has to be treated with two guide wires, before turning back to the former branch. In other use cases, the clinician may treat a chronic total occlusion (CTO) using both, an antegrade and retrograde guide wire. These and similar interventions require at some point the presence at the lesion of more than one device.

In the course of these difficult and demanding interventions, the clinician needs to switch from manipulating one guide wire to manipulating another one—either because he or she decides to focus on a different vessel part, or because he or she wishes to use a guide wire with different physical properties.

The guidewires may extend outside the patient and form a system of wires lying on the examination table. A fluoroscopy system may be used to assist the clinician with real time imagery. A real-time video feed (motion picture) may be displayed on a display device on-site in the catheter lab. The video feed reveals transmission footprints of the introduced devices. Although the clinician may know from looking at the video feed which device he or she wishes to operate, it may not be obvious which device corresponds to which footprint as shown in the video feed.

The clinician may end up picking up the wrong guidewire for example. But such a wrong pick may be highly undesirable. The earlier positioning of some of guide wires may have been difficult enough. The clinician may have struggled for minutes to pass a stenosis or a bifurcation, or to find a fairly stable "parking" position, and then see the perfect parking position lost because of a wrong pick. Specifically, if the clinician indeed unintentionally operates wrong guide wire to start the next stage of the intervention, he or she may unintentionally dislodge the guidewire. This unfortunate event, even relatively rare, is very frustrating. The tedious positioning has to be performed all over again.

Some operators may intentionally shape, e.g. twist, in an "exploratory" effort, the tips of the guide wires before insertion to obtain a shape "signature". But handcrafting the signatures in this manner may be cumbersome and time consuming and may not easily fit into clinical workflow.

SUMMARY OF THE INVENTION

There may therefore be a need for improved support for image-based navigation and to address at last parts of the above mentioned shortcomings.

The object of the present invention is solved by the subject matter of the independent claims where further embodiments are incorporated in the dependent claims. It should be noted that the following described aspect of the invention equally applies to the method, to the computer program element and to the computer readable medium.

According to a first aspect of the invention there is provided a system for supporting image-based navigation, comprising:

an input interface for reviving one or more input images acquired by an X-ray imager whilst two or more medical devices are present, at the same time or at different one or more times, in a field of view of the X-ray imaging apparatus;

an image identifier configured to identify the two or more medical devices based on image information in the one or more images, the image identifier thereby capable of distinguishing between the two or more devices;

a tagger configured to associate respective tags with each of at least two of the two or more medical devices so identified; and a graphics display generator configured to effect displaying on a display device the one or more input images in a video feed, with the tags included; wherein at least one further input image is received at the input interface, and the graphics display generator is configured to effect displaying on the display device only when the image identifier re-identifies in the at least one further input image at least one of the medical devices, the said one or more further input image as part of the video feed, thereby including the same tag as earlier associated by the tagger with the said at least one medical device In other words, the tagging by the tagger as proposed herein is such that any given one of the two or more devices has its own such tag, and the same tags is maintained throughout the whole video feed, or at least a part thereof.

The detector may use image structure filters with thresholding or a machine learning algorithm. The detector may include a segmentation operation but finding a bounding area such as bounding box may be sufficient in some cases.

Not all devices may be necessarily present in a single input image but their presence may be distributed across more than one input image.

According to one embodiment, the identifier includes a detector module configured to detect transmission footprints in the input images caused by the presence of the two or more devices in the FoV.

According to one embodiment, the tagger is configured to implement a clustering algorithm to process the detected transmission footprints into clusters, each cluster corresponding to one of the two or more medical devices.

According to one embodiment, the tagger is capable of changing the number of clusters in dependence on whether a new medical device is present or at least one of the two or more medical devices is removed.

According to one embodiment the association operation by the tagger is based on one or more features, the said one or more features including any one or more, of a combination of: a respective shape of the detected footprints, a current respective image position of the detected footprints, a current anatomical location of the respective medical device.

According to one embodiment at least two of the two or more input images or of the at least one further input image is acquired at different imaging geometries.

According to one embodiment the tagger is configured to selectively adjust an influence of one or more of the one or more features on the association operation, in dependence on a change of the X-ray imager's imaging geometry.

According to one embodiment the input images are projection images.

According to one embodiment at least one of the two medical devices is a guidewire.

In another aspect there is provided an arrangement, comprising: a system as per any one of the above embodiments, and the imaging apparatus and/or the display device.

In another aspect there is provided a method for supporting image based navigation, comprising:
  receiving one or more input images acquired by an X-ray imager whilst two or more medical devices are present, at the same time or at different one or more times, in a FoV of the X-ray imaging apparatus;
  identifying the two or more medical devices based on image information in the one or more images, the image identifier thereby capable of distinguishing between the two or more devices;
  associating a respective, unique, tag with each of at least two of the two or more medical devices so identified; and
  displaying on a display device the one or more input images in a video feed, with the tags included;
further comprising:
  receiving at least one further input image and,
  displaying on the display device the said one or more further input image as part of the video feed only when in the at least one further input image at least one of the medical devices is re-identified, thereby including the same tag as earlier associated with the said at least one medical device.

In another aspect there is provided a computer program element, which, when being executed by at least one processing unit, is adapted to cause the processing unit to perform the method.

In yet another aspect there is provided a computer readable medium having stored thereon the program element.

The proposed system and method allow to make the association between devices and their footprints more explicit. The above described prior exploratory movement of in-situ devices can thus be avoided. Each footprint is tagged with an identification code, persistently and consistently associated with each medical device. There is also a reduced risk that the operator picks the wrong device and unintentionally dislodges it.

Each device is associated with its respective tag, an identification code, that remains the same all over the intervention. Typically, the tag codes which guide wire has been introduced first, in order to match the guide wire order as present on the examination table. The tag may include for instance a number displayed in spatial association with the respective guide wire footprint on the screen. Instead of such a numbered code, or in addition thereto, a color-code may be used: for example, the first introduced guide wire is displayed in red, the second in blue, etc.

This visual help makes the metal connection "guide wire tip on the screen"/"guide wire body ordered on the table" much more straightforward, allowing the clinician to reliably switch guide wires with minimal mental effort.

The "tag" can be explicit by an annotation in form of a box widget or other, optionally including text or graphics, or the tag is implicit, such as through color coding the footprint, border line type variation (bold, dashed etc.), or a combination of the foregoing, or any other visual scheme.

"Detection" as used herein may include a "segmentation". Segmentation aims at tracing the exact delineation of an image object such as a transmission footprint. However, the footprint detection may not necessarily rely on a segmentation as merely finding a bounding box that includes the footprint without necessarily tracing its boundary may be sufficient in some circumstances. Certain features, such as in-image position may be extractable from such a bounding box.

"Adjust influence": this may be achieved by adjusting weights of a cost function. The weights determine how much a comparison in relation to a given feature is to contribute to the overall cost.

"Imaging geometry": in fluoroscopy, this may include angulation angle, rotation angle etc. In general, any setting that changes position or orientation of the optical axis, the imaginary axis that connects X-ray source and X-ray detector.

"User", as used herein, is someone who operates the imaging apparatus or who uses the imagery for navigation purposes as an aid to position a medical device in the patient.

"(Transmission) footprint" is an image portion in a projection image that corresponds to the "shadow" of an object when exposed to X-radiation from a given direction after transmission of the X-radiation through the object.

BRIEF DESCRIPTION OF THE DRAWINGS

Exemplary embodiments of the invention will now be described with reference to the following drawings, which are not to scale, wherein.

DETAILED DESCRIPTION OF EMBODIMENTS

Figure 1:
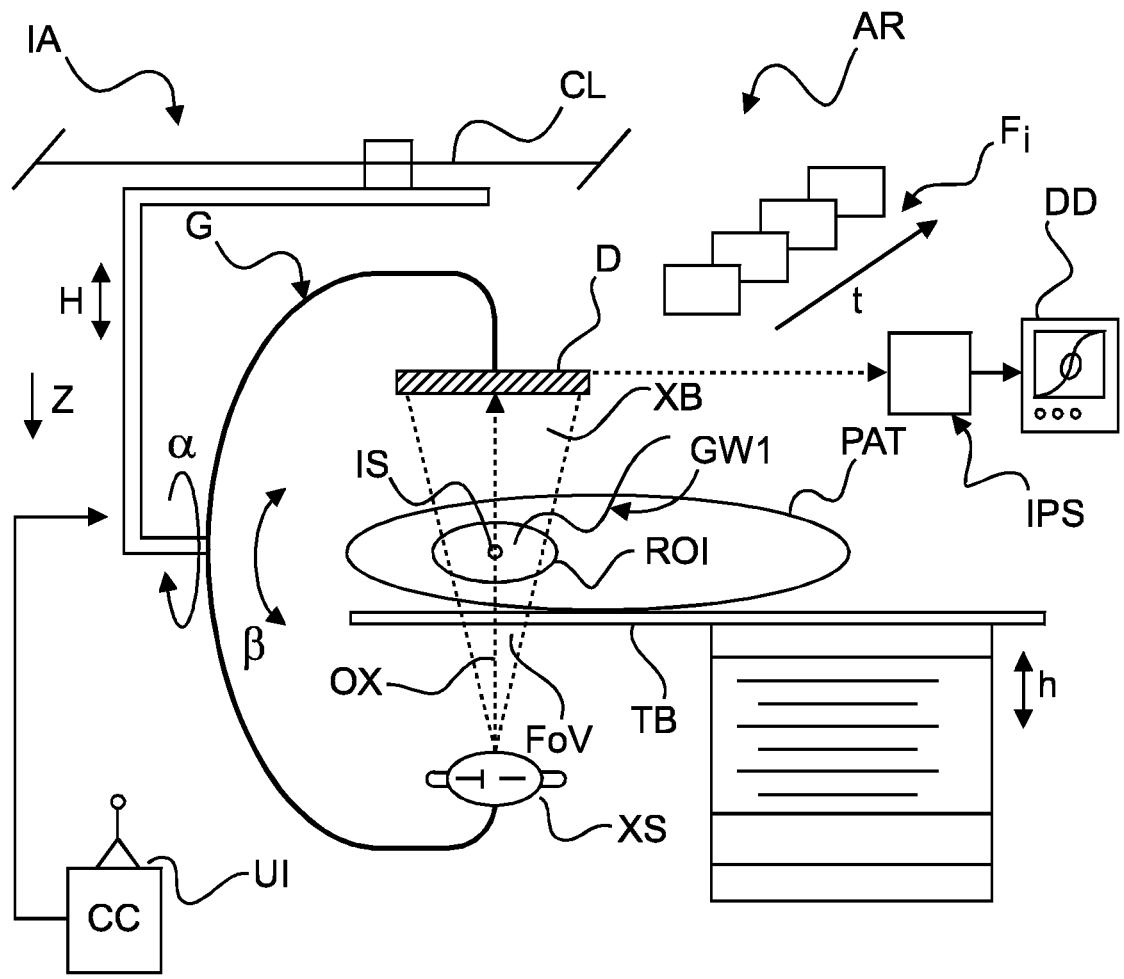
FIG. 1 is a block diagram of an imaging arrangement including an X-ray imaging apparatus.

With reference to FIG. 1 there is shown a schematic diagram of an arrangement AR for image-based support of navigation, for use preferably in the context of a medical intervention.

The arrangement AR comprises, an imaging apparatus IA, in particular an x-ray imaging apparatus, operable by a user to obtain x-ray imagery $F_i$ of internal structures of a patient at a region of interest ROI. The region of interest ROI may be the human heart, the lungs or another organ or groups of organs.

The imagery $F_i$, sometimes referred to herein as a sequence of frames, may be displayed in real-time as a motion picture or video feed on a display device DD to the user.

The imaging arrangement AR further comprises an image processing system IPS to process the imagery. Broadly, the image processing system IPS is a computerized system that processes the received imagery to include therein one or more visual indications or tags that represent respective one or more medical devices. The medical devices are deployed in an intervention. One or more of these devices GW1 may be present at times in a field of view FoV of the imager whilst the images $F_i$ are taken. Not all of the one or more imaging devices may be present in each image. Because of the tags as provided by the IPS, the user can easier distinguish in the displayed imagery, which image portion (transmission footprint) corresponds to which medical device.

As mentioned, the imaging apparatus AI and the imaging processing system IPS are mainly envisaged herein in embodiments to support medical interventions such as percutaneous coronary interventions (PCI). Other medical interventions, not necessarily performed in relation to the human or animal heart, are also envisaged, and so are non-medical applications such as image-based support for examinations and works carried out in inaccessible caving or plumbing systems, or examination of technical equipment such as engines and other complex machinery that cannot be directly inspected by the unaided eye, but require imaging equipment to make occluded regions of interest accessible through a video feed to visual inspection.

In PCI applications, the medical devices may include in particular one or more guide wires that are introduced into the patient PAT through one or more suitable access points such as a cut in the femoral artery or vein at the groin region. The so introduced guide wire is then carefully advanced through the blood vessel to arrive at a lesion site, such as a stenosis in a certain portion of the patient's coronaries. Once a tip portion of the guide wire passes the lesion site, it is fixed ("parked") there, and a catheter or other tool is then slid along the guide wire to the lesion site to perform a procedure. One such procedure may include treating the stenosis by using a balloon catheter to relieve the stricture. Other guide wires, catheters or other medical tools may be additionally introduced into the patient through the same access points or different access points. The coronaries are a complex system of branches and sub-branches of blood vessels. In order for the user to successfully navigate the guide wire to the lesion site, navigational support is provided by the acquired imagery which is displayed in real time as a video feed or a motion picture on the display device D. This allows the user to observe the position of the one or more medical devices inside the patient as the devices are advanced through the patient or whilst the intervention is performed.

Referring now briefly in more detail to the imaging apparatus IA, this may be arranged as shown in the exemplary embodiment in FIG. 1 as an imaging apparatus of the C-arm type. In the embodiment of FIG. 1, the C-arm system IA is ceiling CL mounted but this may not be necessarily so in all embodiments. Alternatively, the imaging apparatus IA is floor mounted, or mounted on a stand. In further alternative, the imaging apparatus may be mobile, such as wheeled or track-mounted.

The X-ray imaging apparatus includes an x-ray detector XD and an x-ray source XS. Broadly, in embodiments, but not necessarily all embodiments, the imaging apparatus comprises a gantry G which carries the x-ray detector XD and the x-ray source XS, such as an x-ray tube. The x-ray detector and the x-ray source XS are arranged on the gantry G in opposed spatial relationship to form an examination region between the x-ray source and the x-ray detector. It is in this examination region that the patient PAT is situated so that the region of interest is positioned roughly at an iso-center of the IS imaging apparatus. The patient may lie on an examination table TB during the imaging. The table may be adjusted in height H.

During the imaging procedure, the x-ray source XS is energized by applying a cathode current and a voltage across an anode and the cathode to produce an x-ray beam XB that issues forth from a focal spot of the anode. The beam exits the x-ray source, passes through the examination region, and hence through patient tissue at and around the region of interest, to then impinge on an x-ray sensitive surface of the x-ray detector XD. The x-ray sensitive surface of detector may comprise pixel elements that convert the impinging x-radiation into intensity values. The intensity values may vary from location to location, the variation being caused by differential attenuation of the x-ray beam due to tissue or tissue types having locally different material densities.

The intensity values so recorded at the detector XS may be mapped into image values according to a color or grey value palette to form a projection image ("frame"). Acquisition circuity operates to capture in this manner at a suitable frame rate a sequence of different projection images at different instances during the imaging procedure. Exemplary frame rates envisaged herein are 20-30 fps. In fluoroscopy, as the main modality envisaged herein, intensity values may be mapped on a range of values ranging from black through grey values to white, with image values the darker the lower the intensity values. Other mapping schemes may be used, such as a reverse mapping, where lower intensity values are mapped to lighter image values such as is commonly used in radiography. Still other mapping schemes may be used instead.

The spatial width of the primary x-ray beam defines the field of view FoV of the imager IA. Objects that reside or extend into the field of view, and hence into the x-ray beam, will modify the intensity with which the x-ray is detected locally at the detector. The field of view may be changed by user request such as by moving the X-ray source, moving the patient, or by enlarging or restricting the beam width by using a collimator (not shown).

The X-ray detector may be arranged as a digital flat-panel detector communicatively coupled to the display device DD. The flat-panel detector XD may be of the direct conversion or indirect conversion type. In an alternative embodiment, the imaging detector may be arranged as an image intensifier coupled through a video camera to the display device.

Although the contrast conferring mechanism of the projection imagery mainly envisaged herein is attenuation, other imaging techniques that exploit, in addition or instead, other contrast mechanisms are not excluded herein such as phase contrast and/or dark-field imaging. In the latter two cases, the imaging apparatus may include additional components, such as an interferometer or other.

The imaging apparatus includes a control console CC through which the user can determine when to start and stop the imaging procedure, in particular when to energize the x-ray source XS. A pedal may be coupled to the console as a user interface to control energizing or de-energizing the x-ray source or to operate a grid switch to halt or resume exposure to the X-ray beam.

The main propagation direction of the primary x-ray beam (leaving aside scattered radiation) is defined by the optical axis OX which is an imaginary line that runs from the focal spot (not shown) of the x-ray source to a center portion of the x-radiation sensitive surface of the x-ray detector XD. The optical axis defines the spatial projection direction.

In order to better support the user in navigation, a position or spatial orientation of the optical axis, and hence of the projection direction, may be changed on user request. This can be achieved in one embodiment by arranging the gantry to be rotatable around one, or preferably two, respective axes perpendicular to each other. Having two such rotational axes allows for 2 degrees of freedom for changing the optical axis. For instance, in one geometry one of the rotation axis extends into the drawing plane of FIG. 1 and allows the optical axis to be rotated around an angle β. The other rotation axis is parallel to the drawing plane of FIG. 1 and allows changing the orientation around another angle α, independent of β, as schematically shown in FIG. 1. By convention, the axis for α defines "the rotation" whilst the axis for β defines "the angulation".

Optionally, it is also the height of the gantry itself that may be changed as indicated by double arrow H in FIG. 1. In addition, the optical axis OX may be translated by moving the gantry accordingly along a line. Position and orientation of the optical axis may be referred to herein to at least partly define the imaging geometry. In other words, the imaging apparatus envisaged herein in embodiments allows the user to change the imaging geometry. The change of the imaging geometry may be requested through the user operating a joy-stick or other suitable interface means coupled to the control console CC. Operating the interface for requesting the change in imaging geometry may include causing control signals to be applied to suitable actuators arranged in relation to the gantry. The actuators act in response to the control signals to change the imaging geometry.

Other options to change the imaging geometry may include changing the detector-x-ray source distance and/or changing the distance between the region of interest and the x-ray detector and hence the x-ray source. The latter change may be effected by changing the height h of the examination table TB on which the patient lies. Changing height h and/or the source-detector distance may amount to a rescaling of the image at a certain magnification factor. Yet other options to change the imaging geometry may include operation of the collimator (not shown) to restrict or enlarge the cross section, in shape or size, of the x-ray beam to change the field of view FoV. Yet another option to change the imaging geometry may include translating the patient table TB in a plane parallel to the surface of the table in X,Y direction, one direction being parallel to the drawing plane of FIG. 1 and the other extending into the image plane.

In general, and to summarize, a change in geometry changes the spatial relationship between the x-ray source and/or detector relative to the region of interest. In addition or instead, the field of view may be changed by collimator action or by moving the patient for instance by table TB translation as described.

As mentioned earlier, for fluoroscopy, it is not usually a single image that is acquired but a series or stream of images or "frames" $F_i$. This stream of frames $F_i$ may comprise for present purposes different sequences of such frames. A sequence of frames is defined for present purposes as one where all frames in the sequence have been obtained in a single imaging geometry, in particular position and/or orientation of the optical axis has not been changed during the sequence. In a typical protocol then the user will energize the x-ray source and acquire a sequence of images at a given imaging geometry, whilst the sequence of frames is displayed, one after the other, in the video feed on the display device. The user may request the imaging to stop, that is the x-ray source is de-energized or the x-ray beam is otherwise disabled, for instance by collimator or grid switch action. The imaging geometry may then be changed, for instance by the user choosing a different angulation. The X-ray beam is then re-enabled and/or the x-ray source is re-energized to acquire a second sequence of frames, this time at the second imaging geometry, and so forth for three or more different such sequences. The whole imaging procedure may then comprise one or more different image sequences where the imaging geometry of two contiguous sequences may be different. It may be the case that all sequences in the imaging procedure are acquired at different imaging geometries although this may not necessarily be the case as in some sequences, even contiguous ones, the same imaging geometry may have been retained.

Figure 2A:
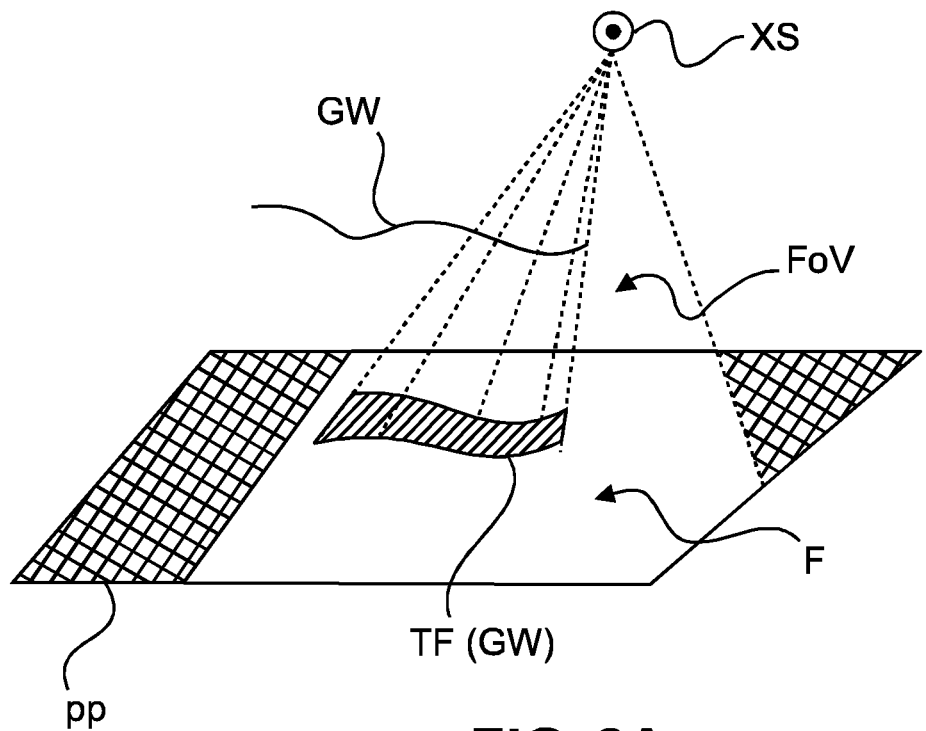
FIG. 2A is a plan view on a part of the imaging arrangement.

Referring now to FIG. 2A, this illustrates the manner in which image information is encoded in a recorded X-ray frame F. The medical device GW such as, for example, a guide wire may reside in the field of view FoV of the imager IA. The x-ray beam XB emanates from the x-ray source XS and interacts with the guide wire. Because of the guidewire GW's radiation opacity, the x-ray beam is attenuated. The attenuation so experienced is higher compared to the attenuation caused by surrounding tissue. This differential attenuation leaves a pattern of intensity values that corresponds to the shape of the guidewire when viewed along a given projection direction as per the currently set imaging geometry. This pattern of intensity values so produced may be referred to herein as a transmission footprint TF(GW) or "shadowgraph" for the specific medical device as schematically drawn in FIG. 2A in the projection plane pp of the detector XD in the given imaging geometry.

If the surrounding tissue is soft tissue, such as blood vessels, their respective transmission footprints may be recorded only in very low contrast. If required, soft tissue contrast can be given a boost by administering contrast agent. Frames acquired during the presence of contrast agent at the region of interest may be referred to herein as angiograms. In addition or instead, the "roadmapping" techniques may be used where the vessel borders are graphically indicated by overlaying lines that represent the vessel tree. Contrast agent supported 3D imagery earlier obtained for the patient or a generic vessel model, possibly personalized to the patient, may be used after suitable registration to the fluoroscopy frames to effect roadmapping. Roadmapping is described for instance in Applicant's U.S. Pat. No. 8,255,037. However, relying solely on the contrast conferred by the transmission footprints of the devices, possibly with an occasional contrast agent administration, may be sufficient at times to support the navigation, so an explicit roadmapping may not be required.

Figure 2B:
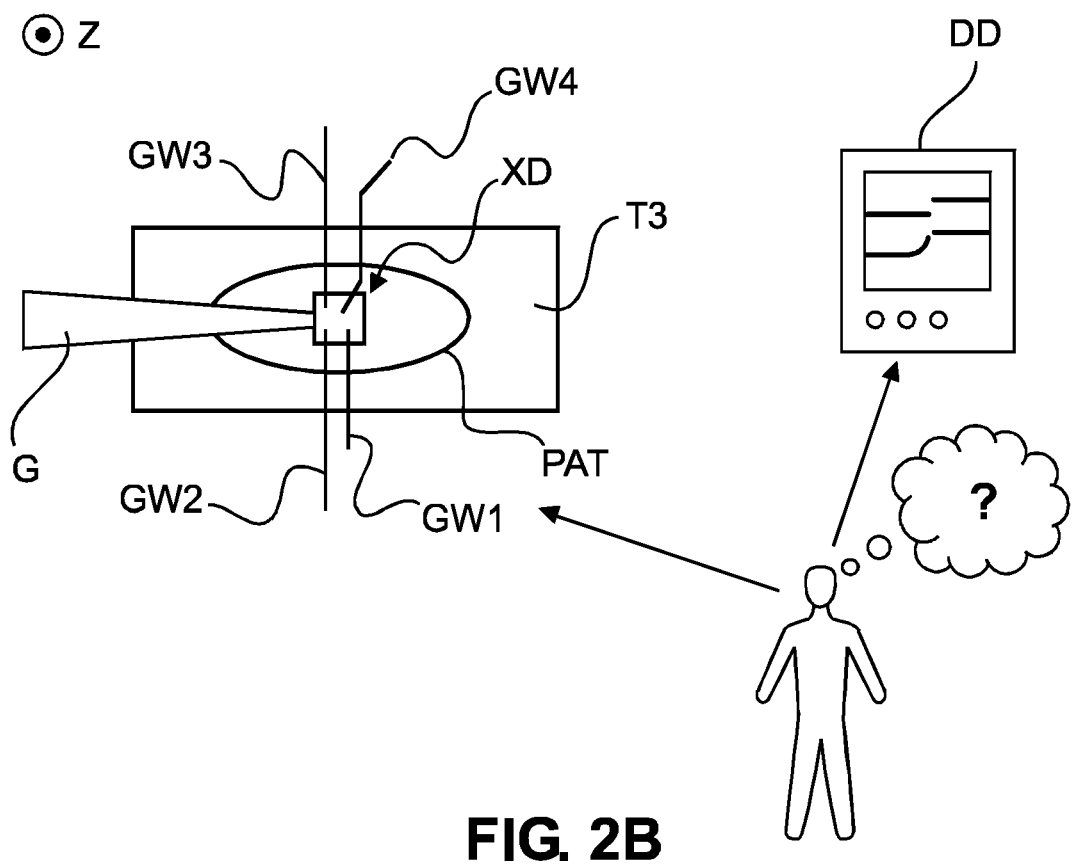
FIG. 2B is a schematic diagram of a transmission footprint recordable in an X-ray projection image.

A situation frequently faced by the user is that it is not just one medical device that is used, but a plurality of 2, 3, 4 or more devices of one or more types are employed and introduced into the patient. Four such devices GW1-GW4 are shown schematically and exemplary in the plan view of FIG. 2B. A given image frame as shown during the video feed on the screen DD may hence comprise a pattern of a plurality of transmission footprints for the plurality of devices GW1-GW4, and the user may be at a loss as to which device GW1-GW4 corresponds to which transmission footprint in the displayed frames. The arrangement of devices GW1-GW4 in FIG. 2B is for illustration purposes as in practice most devices will have been introduced through the same access point. Still, in a certain narrowly focused, "tight", collimation setting for example, a representation of footprints similar to the one shown in the display device DD in FIG. 2B (and further below in FIG. 6) may well result.

The proposed imaging apparatus IPS allows addressing this concern by tagging the respective image footprints in each frame in a consistent manner throughout all sequences for the imaging procedure. The tagging may be graphical or textual. The tagging may be explicit or implicit. Implicit graphic tagging may include for instance displaying the respective shadowgraphs in different colors or having them outlined in different line types such as dashed, dotted or otherwise. In addition or instead, explicit tagging may be used by displaying a graphical widget such as a box, a triangle, a circle, an ellipse or any other geometrical shape in spatial association with the respective transmission footprint. The explicit tag may also include textual material that may indicate the chronological order at which the respective device has been introduced into the field of view. In addition or instead, the textual information may include suitable acronyms or full names, or some alpha-numeric string, that provide the user with a clue as to which type of medical device the respective tag is associated with. Alternatively, the tag may simply include a respective, distinct alphanumeric string to support a better distinction, not necessarily tied to a particular semantic.

Figure 3:
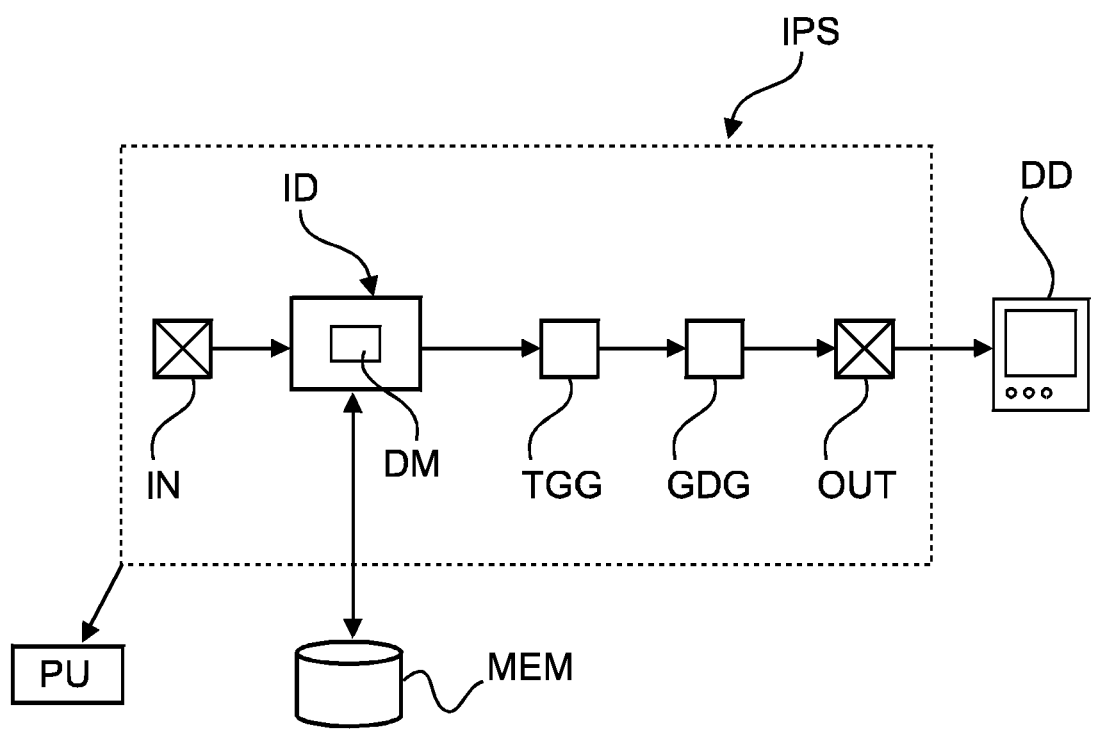
FIG. 3 is a block diagram for an image processing system configured for supporting image-based navigation.

Operation of the image processing system IPS will now be explained in more detail with reference to the block diagram of FIG. 3. Broadly, the image processing system IPS is configured to perform image based transmission footprint tagging that is consistent throughout different geometries and is preferably persistently associated with an individual, respective one, of the medical devices.

The imaging processing system is computerized. It may be implemented on a single or multiple data processing systems PU. The processing system(s) implementing the image processing system is diagrammatically and schematically shown as PU in FIG. 3. The IPS is either integrated in the imaging apparatus IA or is otherwise communicatively coupled, in a wired or wireless manner, with the imaging apparatus IA that supplies the frames $F_i$.

The imaging processing system IPS may be arranged as one or more software modules suitably linked and run on the one more processing units PU. Alternatively, the imaging processing system IPS may be arranged in hardware as a suitably configured micro-controller or micro-processor. The image processing system may be implemented in a distributive fashion by a plurality of communicatively coupled processing units. The image processing unit may be arranged partly in hardware and partly in software. Some or more of the following described components of the image processing system IPS may reside in one or more memories MEM suitably communicatively coupled. The data processing system PU may be a general purpose computing device suitably programmed. The processing unit may include a graphical processing system (GPU) to achieve speedy computation.

The imaging processing system IPS includes an input port IN for receiving the imagery $F_i$. The imaging processing system IPS includes an image identifier ID to identify one or more of the medical devices that may happen to reside in the FoV during imaging. The identifier ID may include a detector module DM to detect transmission footprints of the devices GW1-GW4. The identification operation by identifier ID is based on the detected transmission footprints TF, if any.

The image identifier ID attempts to identify the medical device(s) based on the detected transmission footprints in the imagery as received at the input port. As will be explained in more detail below, the identifier ID is configured to perform this identification operation consistently across the imagery, particularly across changes of imaging geometries. The image detector may also be configured to detect when devices are removed from the field of view and/or earlier devices are re-introduced into the FoV, or, if new, not previously seen, device(s) are introduced into the field of view during the imaging.

There is also a tagger TGG to tag the detected footprints once the footprints have been identified to belong to new or previously identified respective medical device. Tagger TGG associates with each footprint, that is found to identify a given device GW, a unique tag that remains with the individual device GW.

The imagery with one or more tags as provided by the tagger, if any, are then processed by a graphical display generator GDG. For each given frame, one or more tags are integrated into the received imagery, for instance as overlays, or otherwise.

The so tagged imagery is then output at output port OUT. The tagged imagery may then be displayed on the display device DD by suitable graphics control circuitry to build a video feed from the, possibly tagged, imagery.

More specifically, a given tag is included into the processed imagery only if the respective device is actually identified by the identifier in the given frame. The device may have been recorded in one frame but not in another. Accordingly, its tag is or is not included into the respective frame.

Operation of the image identifier ID is event driven. The events include, a change in the number of devices in the FoV, a change of a type of GWs used, and or a change in imaging geometry. The identifier ID acts dynamically and adaptively to adapt to said events. An algorithm as implemented by the identifier ID may be adapted in response to any one or more of these events. In embodiments a cluster algorithm is used. The identifier ID acts preferably conservatively to assign and define a new cluster given one or more existing clusters: an attempt is made to assign detected footprints into existing one of the clusters. Only if this cannot be achieved at a reasonable cost, as measured by a suitably configured cost function in the context of a minimization scheme, a new cluster is declared.

Optionally, the image processing system may include circuitry arranged to detect when a change in imaging geometry has occurred.

In general, operation of the detector module of the identifier ID may include segmentation by the detector module of the recorded footprints, if any. The segmentation part can be solved by manually handcrafting computer vision processing tools, such as elongated filters, and thresholding. Instead, machine learning may be used such as marginal space learning (MLS) as reported for example by Zheng Y et al in "*Marginal Space Learning for Efficient Detection of 2D/3D anatomical structures in Medical Images*", Inf. Process Med. Imaging, vol 21, pp 411-422, 2009. Deep learning architecture neural networks, that is, neural networks, with one or more hidden layers are also envisaged. Preferably of the neural networks are of the convolutional type.

The clustering of the resulting segmentations can be performed by associating similarity comparison of footprint segmentations in two successive frames. The comparison may be based on spatial distance between in-image positions of the two footprints from different frames, as it is expected that this distance is small if both segmentations correspond to the same guide wire. In addition or instead, other features may be evaluated for similarity, such a geometrical shape of the footprints. Given the same imaging geometry is used (which is not necessary herein as will be explained in more detail below), the footprint shapes can be expected to be similar to each other if the footprints from the two frames do correspond to the same device. Comparison of shape and in-image position should be used in combination in order to resolve ambiguities that may arise if devices with the same or similar shape features are used as any two devices may rarely be expected to reside at the exact same position. An optimization method (for instance, dynamic programming) can be exploited to determine which labelling provides the best similarities between associated segmentations. The segmentation and identification should be preferably performed in quasi-real-time for better user experience. GPUs may be used to achieve such quasi-real time processing.

Figure 4:
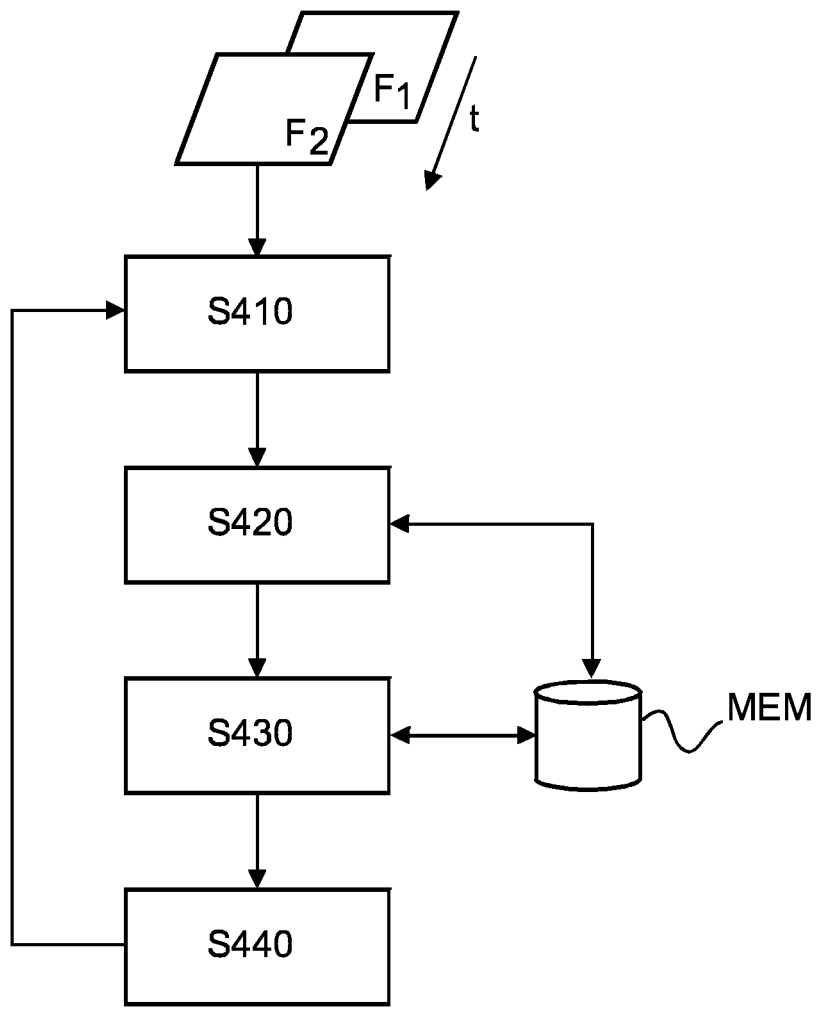
FIG. 4 is a flow chart of a computer implemented method for image based navigation support.
Figure 5:
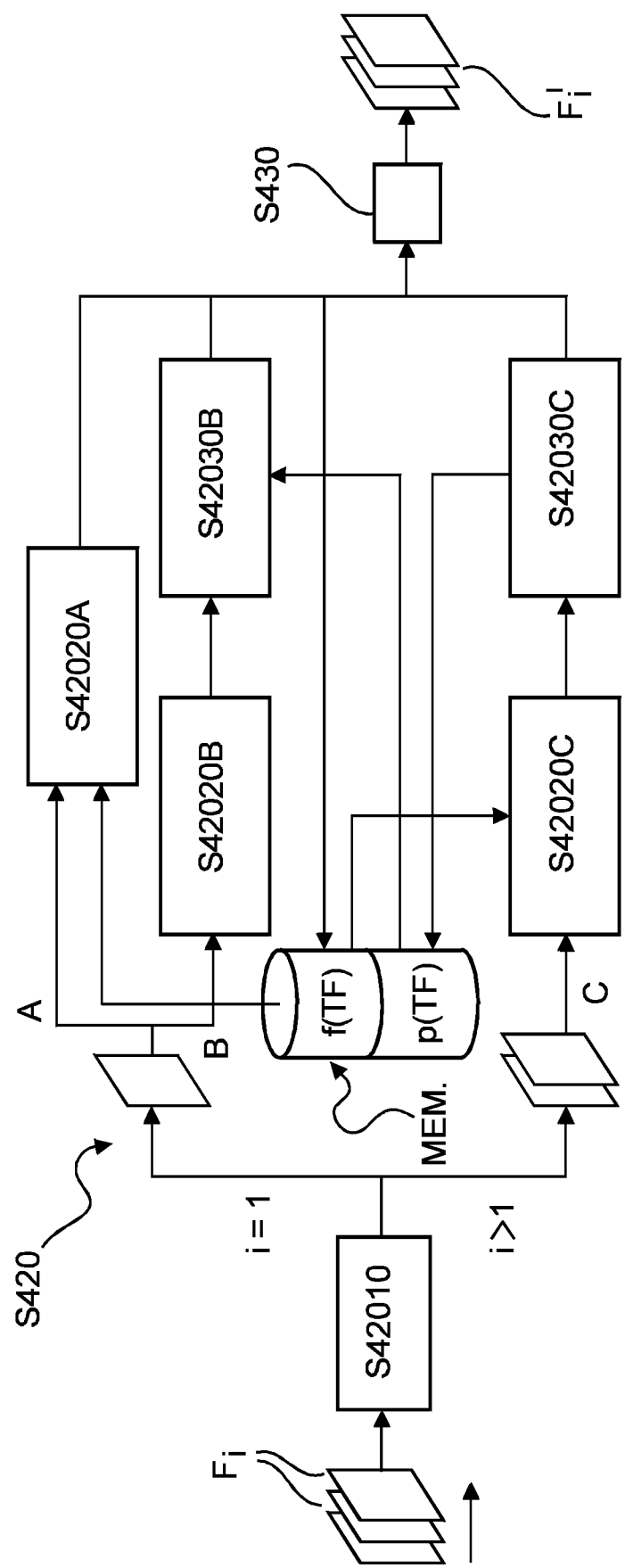
FIG. 5 is a flow chart providing further details of the method in FIG. 4.

Reference is now made to the flow chart in FIG. 4 where a method for supporting image based navigation is explained in more detail. The method may be understood to underlie operation of the above mentioned image processing system IPS. However, it will be further understood that the method steps explained in FIGS. 4, 5 are not necessarily tied to the architecture of the image processing system IPS as described above in relation to FIGS. 1-3. More particularly, the method described below may be understood as teachings in their own right.

In step S410, frames are received as acquired by the x-ray imaging apparatus IA in a sequence.

During acquisition of these one or more frames in the sequence, two or more medical devices such as the mentioned guide wires, catheters or other tools were present in the field of view of the imaging apparatus. However, for present purposes it is not required that all of the medical devices were present together at any given time but may have been present separately at different times of the acquisition. In other words, the medical devices may have been recorded across two or more of the frames rather than all devices being recorded in a single frame which is also envisaged of course in embodiments. For instance, one frame acquired at a certain time may have recorded two or more, in particular, all of the medical devices currently in use. Alternatively, however, one or more of the devices have been recorded in one frame whilst one or more of the other devices have been recorded in different one or more frames. The presence of the devices may change, because the user may decide to remove one or more of the devices from the field of view or the user may choose an imaging geometry setting, such as collimator setting or a tube XS angulation/rotation, so that one or more of the devices are no longer in the new FoV, etc.

In step S420 an attempt is made to computationally identify the medical devices based on image information as encoded in the received frames. The identification operation is such that the different medical devices can be distinguished from each other. The image information that is used for this identification operation includes in particular the transmission footprints as encoded and recorded in the frames.

The identification step S420 itself may include two sub-steps. One is the detection of the image footprints themselves as image structures in the one or more frames. The detection can be done by a segmentation. Segmentation may be done by computer vision techniques, such as machine learning, filtering or an intensity value thresholding or others. However, segmentation is not a necessarily requirement, as in some cases it may sufficient to establish an area, such as a bounding box, circle or other, and to the analysis statistical information for pixels within the area, such as histograms, standard deviations, CV, etc. The exact course of the border of the footprint may not be necessarily required in all embodiments. At this sub-step, there is not yet an association of the footprints to the respective medical device that caused the transmission footprints.

The identification or association of the detected footprint-versus-medical device is carried out in the second sub-step of the identification step. The second sub-step of identifying the devices themselves with the respective footprints may be implemented by a clustering algorithm. The clustering algorithm clusters the footprints into groups where each group represents exactly one single one of the medical devices.

This second-sub-step of the identification step S420 will be explained in more detail below and is based on certain image features extractable in relation to the identified footprints and/or on contextual information. In particular, information about the change of imaging geometry may be used to inform the clustering operation. Other features that may be used in combination or singly include geometrical shape or size, in-image position, or anatomical position. The features may be stored in memory MEM in association with the respective cluster. Some or all of the so pre-stored features may be retrieved when performing the clustering in the next frame, and so on.

It may be sufficient in the identification operation at step S420 to identify merely a part of the footprint and to compute features in relation to this part only. In embodiments, it may be useful to consider a neighborhood around where the footprint terminates as this section represents the device' tip portion, such as the guidewire tip, and this part is in general the clinically relevant one. Other features may computed in relation to whole of the footprint.

In the following step S430 a respective unique tag is then associated with each respective medical device identified in step S420.

Each tag may be represented as visually distinguished from the other tags and may be represented by a graphical widget as mentioned above. The type, color coding, etc. of the tag may be specified by the user beforehand in a set-up operation. For example, a menu structure in a graphical user interface may be presented to the user to choose the tag style. As mentioned earlier, the tagging may be explicit or may be implicit. Implicit tagging may include color coding identified footprints and or changing contours by color- or line-type (dashed, doted, etc.) coding.

Explicit tagging may include adjoining in spatial relationship with the respective footprint, a separate, discrete, information box, circle, ellipsis or other geometrical structure widget. The tag widget may or may not include textual information that allows the user to better identify the identity of the tagged device when the tag is included in the image.

At step S440 the received frames are displayed on the display device as a video feed (motion picture) with the tags included. In particular, this may entail overlaying the graphical widgets into the image suitably positioned in spatial association with their respective transmission footprint and hence device.

The identification operation S420 may be based on image features which may be stored in memory and are retrieved there from when processing follow-up frames in a similar manner.

It is envisaged herein that the tags associated with the respective devices are persistent or remanent throughout the imaging procedure. In particular, one specific tag remains associated with a specific unique imaging device throughout the imaging procedure. In more detail, if a follow-up frame is received this is processed as described above but the tag for a given medical device will only be included into that frame if that medical device is positively identified in the follow-up frame. If it is not identified, because the user has removed the device from the FoV or the FoV has been changed due to an imaging geometry change, then the tag for that device will not be integrated into that frame. If, however, the device is then later identified in a later follow-up frame, its tag is then included into that later follow-up frame.

Equally, if a new device is introduced, a new cluster may be defined to accommodate the newly introduced device, and a new tag will be associated with the newly introduced device. The new tag is different from all other tags previously assigned to other devices. Removal of a device from the FoV may occur for instance when the user "pulls" the device, e.g. a guidewire, out of the field of view FoV, in particular, remove the device entirely from the patient. A certain given device may not be recorded in given frame if an imaging geometry change occurs such as for instance the table TB is moved and/or a collimator restricts the field of view, or if the X-ray source is repositioned by the user requesting a new angulation or rotation, or translation, or a combination thereof.

In sum, if one of the devices is removed from the current FoV, or a new device is introduced in the FoV, or if a known device that was not in a previous FoV but is re-introduced into the current FoV, the number of clusters as defined by the identification step is dynamically adjusted accordingly for the given frame as recorded for that FoV. In other words, as will be understood from the above-mentioned use cases, the identifying step and the tagging step are event-driven operations, and dynamically adapted to the actual image content in any given frame.

The identification operation may be implemented in the context of a numerical optimization procedure. In particular, the clustering operation may be formulated as an optimization procedure to optimize, for instance minimize, a cost function which is associated with the clustering. The cost, that is the scalar value of the cost function, is expected to stay relatively stable if the number of devices as recorded in the frames remains constant but is expected to change appreciably when devices are removed from the FoV or a new device is introduced, or a known device reappears. This sudden change of the cost may provide an indication that the number of clusters to be considered needs to be either increased or decreased. In other words, the adaption of the number of clusters may be done fully automatically. This event may be called henceforth as a "disturbance of numbers" and indicates an event that a medical device has either been removed or (re-)introduced into the field of view.

Another indication for a disturbance of number event is a change of the number of detected footprints. The number of clusters will generally correspond to the number of image footprints as detected in the frames. This number may be monitored and if there is a change from one frame to another, the optimization procedure attempts to change then number of clusters accordingly. A local analysis may be performed. For instance, if there was a footprint in a certain region of an instant mage, and then there is no footprint any more at the corresponding area in a follow up image, the cluster number may need to be adapted.

Optionally, the user may provide a signal for instance by pressing a button or otherwise to the algorithm as input. The signal may be used in the identification step to adapt the number of clusters.

It can hence be seen that the identification operation step S420 is robust against disturbance of number events. The step is furthermore robust against changes of the imaging geometry.

The robustness of the identification step S420 is achieved because the operation is based in particular on features that are associated with the identified transmission footprints. The features considered herein include one or more or a combination of the geometric shape as presented in the detected transmission footprints. In addition or instead, an in-image position in the current frame of the footprint constitutes another feature of the transmission footprint. A suitable reference point in the detected footprints may be used to define the position in the image plane of the given frame. Alternatively, barycentric co-ordinates may be computed for the transmission footprint. In embodiments, a terminal, extreme portion of the footprint is identified and this tip of the footprint is then used to define in image location as this corresponds to the location of the physical tip of the guidewire, catheter or other device.

A contextual feature of a given transmission footprint in a given frame is the anatomical location that is associated with the footprint and hence the respective medical device. For instance, as will be explained in more detail below, in change of imaging geometry event, an anatomical location may be used to ensure the persistent and consistent identification of the given imaging device.

The anatomical location may be determined by road mapping techniques or by registering the current frame to a 3D image of the region of interest previously recorded by the same or different image modality. In particular, a CT data set may be used suitably segmented and this can then be registered by forward projection for instance with the current image frame to identify the image location. Alternatively, an artificial model, preferably personalized to a region of interest of the given patient, may be used to compute the anatomic location.

In addition or instead to roadmapping, deep learning may be used, suitably trained using training image data. In the following a number of different embodiments will be described how the anatomical location may be derived through deep architecture neural network based machine learning techniques. However other machine learning techniques, such as support vector machines (SVM), other kernel based methods, or decision trees and others are not excluded herein. The training data is provided in pairs of input and (desired) output.

Machine learning may be used by training based on imagery that represents vessel trees along different projection directions.

In another embodiment, co-registration may be used where a guide wire position is projected on the corresponding angiogram (if it exists), and the so contrast enhanced coronary tree as presented in the angiogram can be segmented and split into its sub-segments to so define anatomical positions. A machine learning component may be used to factor in the imaging geometry change, by training on the following training data pairs: Input: Image or segmentations of vessels in the image and imaging geometry change specification (e.g., angulation). Output: anatomically labelled branches or sub-branches.

In one embodiment, the anatomical location associated with the device GW position is obtained from the fluoroscopic image only. The machine learning component may be trained based on the following input/output pair: Input: fluoroscopic image and geometry change specification (e.g., angulation and current device GW position. Output: anatomical location specification.

Alternatively, machine learning approach is combined with the earlier mentioned roadmapping techniques. More specifically, in a first step, the device GW position is found in an angiogram in, by roadmapping, which is equivalent in this case to co-registration. Then the machine learning approach is applied with the following input/output pairs: Input: angiogram and device position GW, obtained from the fluoroscopic image by roadmapping. Output: anatomical position.

In a further embodiment, more explicit than the previously described embodiment, in a first step roadmapping is used to obtain the device GW position on an angiogram. In a second step, a detection, e.g. segmentation, is performed. The so found branches in the vessel tree in the angiogram are labeled by machine learning. Lastly, braches in the labelled vessel tree are scanned to find where the device footprint GW is positioned.

In a further embodiment, the given device GW footprint is projected into a 3D model of a coronary tree. The model is either generic, personalized, obtained from a 3D image such as a CT volume. The model may be pre-labelled or the labelling is done by machine learning. The projection may be either directly or via angiogram, such as per the following sequence fluoroscopic image→angiogram→model.

In PCI or similar heart related interventions, the anatomical position is defined by the respective sub-vessel (for instance, RCA mid, or LDA distal) in which a guide wire tip lies. Indeed, given a certain imaging geometry, e.g. an angulation, one roughly knows how the projected coronary tree looks like. One may then recognize in which vessel branch a guide wire is navigating into for the next frame, and approximatively at which distal position the guide wire was located. One may then associate the guide wire footprint residing, for instance, in the proximal circumflex as per a current frame of a current sequence, with a guide wire footprint residing in the proximal circumflex as per a frame in a next sequence. Devices that may happen to reside in the same vessel sub-segment can be disambiguated by assessing which one is more distal than the other. Here, "distal" refers to the direction, downstream the vessel, which is the opposed direction ("proximal") from which the device advances.

The one or more features extracted in relation to a given footprint such as shape, in image location and/or anatomical location may be associated and stored in memory with a given footprint for a given frame. The clustering operation may then include comparing the stored features of transmission footprints in one frame with those of a follow-up frame to perform the clustering. The comparing may be performed by a pixel-wise subtraction of one footprint from another in a follow-up frame and to suitably quantify or attach a cost to the difference. A similar comparison by subtraction can be done with the in-image positions and/or anatomic locations, if required.

Instead of comparing features in the image domain, it may be preferable to compare descriptors of the shape of the footprint. In one embodiment this may be superimposing two footprints to be compared by registering. The comparison may then be based on measure of deviation between their centerlines. Suitable measure may include the any one of max/mean/median distance.

Alternatively, the shape of the footprints, e.g. their borders, are represented as respective coordinates (coefficients) over of set of base functions, such as splines. The comparison is then based the said coordinates. Absolute values subtraction or Euclidean distance or any other suitable distance measures may be used.

The comparison with respect to anatomical location may be binary. Either both footprints are in the same anatomical segment (e.g., vessel branch) or not. Neighboring segments may also be taken into account, assuming the device passed, between frames, from a distal end of one segment to a proximal end of the other, neighboring, segment. Anatomical constraints may be enforced to rule out anatomically impossible moves: for instance, it is impossible to "jump" from a left coronary to a right coronary.

The feature comparisons for one or more of the features may be normalized and consolidated into a single cost value to form the cost function. For instance, the partial costs incurred in the different feature comparisons may be summed.

Each clustering may attract an overall cost. The overall cost for different clustering can be computed and the clustering attracting the lowest cost, or a cost lower than a threshold, may then be chosen as the correct clustering. A clustering is defined by assigning all footprints from a pair of frames to clusters. The number of clusters may be used as a further feature, suitably quantified and included into the cost function.

In general, the clustering is performed for all detected transmission footprints for any two pairs of consecutive frames $F_j, F_{j+k}$, k=1, although it may well happen that some frames are skipped because of poor image quality or for whatever reason, and the considered pairs are then $F_j, F_{j+k}$, k>1. The clustering is then performed based on extracted features of footprints in each given pair $F_j, F_{j+k}$, k. Each cluster, which represents a certain device, may in general include at least two footprints, at least one from each of the frame pair $F_j$ and $F_{j+k}$. However, singleton clusters including only a single frame may also emerge, when one of the frames in the pair includes a footprint of a newly introduced or re-introduced device or if device outside the current FoV.

In broad terms, a clustering cost function $f(\cdot)$ may be defined as follows:

$$f(\varphi \to C) = w^p \times \qquad (1)$$

$$\Delta(p(\varphi), p(\chi^C) + w^s \times \Delta(s(\varphi), s(\chi^C)) + w^a \times \Delta(a(\varphi), a(\chi^C)) + w^g \times G(\#C)$$

$$(\varphi \to C)^* = \mathrm{argmin}_{\varphi \to C^i} f(\cdot) \qquad (2)$$

wherein:
  φ a detected footprint in frame $F_i$, χ a footprint of another frame $F_{i+k}$ in a given cluster C. The given cluster resulted from earlier clustering in respect to earlier frames;
  C is a given cluster of footprints from a given frame pair $Fi, F_{i+k}$,
  "φ→C" is an association of φ with a given cluster C,
  p,s, a are the in-image position feature, the shape feature and the anatomical feature, respectively, and Δ is a comparator to define a partial cost. A may be implemented by pixel-wise subtraction, absolute value subtraction, squared subtraction, Euclidean distance or other suitable norms, such as $L^p$, p>2,
  w's the respective feature weights, and
  $G(\cdot)$ is a partial cost for the number of clusters used, possibly suitably normed.

The partial cost for the anatomical term $\Delta(a(\varphi), a(\chi^C))$ may be set to a large value, or infinite, if anatomically impossible move is proposed by the algorithm. In this manner, anatomical constraints may be enforced.

In the optimization, the clustering, that is the assigning of the footprints to clusters, is adapted so that the cost function may be improved. Preferably, a clustering is found so that the cost function $f$ assumes a global or local minimum. The improvement may be achieved in an iterative manner in which the optimization is configured to converge through one or more iterations towards a local or global minimum. It may be sufficient to abort the iterations once a stopping condition has been satisfied. The stopping condition may be implemented as a threshold. If the cost function does not change by more than the threshold, the iterations are aborted and the current clustering is output as the "best" clustering to conclude the optimization. Optimization schemes envisaged herein to solve (1) may include gradient based schemes, such as conjugate gradients, Nelder-Mead, or other. The cost function may not necessarily be explicit. Implicit optimization schemes such as k-means clustering or other machine learning schemes, iterative or not may be used. Other machine learning schemes envisaged include neural networks or support vector machines and others. If the number of devices used is relatively smalls such as 2-3, a purely discrete evaluation of (1) by comparing the cost for each clustering and by choosing the one that minimizes (1) may be sufficient and quick enough in some cases. The number of clusters may be incremented from 1 to a reasonable upper bound that can be set by the user. Capping the number of clusters to be considered in this manner may also be done in any of the above mentioned continuous optimization schemes to reduce search space and hence computation time. Although (1),(2) have been formulated as a minimization of a cost function $f$, this is not limiting as "dual" formulations in terms of maximizing a utility function are also envisaged herein.

The cost function may be adjusted when any of the above mentioned events occur. Specifically, an influence or contribution of some of the individual terms of the weight w function may be adjusted when the events occur.

More specifically, if an imaging geometry change occurs from one sequence to the next the cost function needs to be modified so as to account for the change. The structure of the cost functions however can be maintained for frames in a given sequence.

The cost function $f$ needs to be modified in the case of an imaging geometry change because now there is no longer expected to be a correspondence between shapes and/or in-image locations. This is because, from a different spatial perspective the footprints of the very same imaging device may look completely different and may also be located at a completely different in-image location. In order to account for this, weights can be used to disable or discount in-image and/or shape features and instead emphasize the contribution of the anatomical location. The anatomical location as compared to the other features is, in other words, an invariant that remains persistent even though an imaging geometry change occurred. It will be understood that other such invariants, not necessarily anatomical locations, may be used with benefit to detect and process sequences at different imaging geometries, such as contrast specification or length of the device's tip. The in-image position and the shape are features which are not invariant as these features will change under different imaging geometry. For instance, "top-right" in one frame may correspond to "lower-left" in a next frame after imaging geometry change. Also, the shape feature may change completely for devices that are not completely symmetric under rotation for instance.

By considering features in combination, the robustness against the mentioned events can be achieved, which in turn results in a persistent and consistent tagging.

Reference is now made to the flow chart in FIG. 5 which explains in more detail the identifying step S420 in particular. In particular, the process flow of the proposed method may be adapted based on the acquisition timing of any given frame.

Specifically, at step S42010 it is determined whether a given frame as received at step S410 is the first such frame $F_1$ in the sequence, which is indicated in FIG. 5 by the query "i=1?", or whether the frame is not the first frame for the given sequence indicated in FIG. 5 as query "i>1?".

Turning now to the first branch "A" in the process flow as per FIG. 5 where the given frame is indeed a first frame for the given sequence at a given imaging geometry, it is then determined whether the imaging geometry is the same as in the previous sequence. If yes, the same identification operation based on the same cost function for the clustering may be used and identification can then proceed in step S42020A as in the previous sequence and as explained above in relation to step S420 in the general flow chart of FIG. 4. In embodiments, the cost constraint on in-image distance may be relaxed in between sequences, to account for a possibly larger motion of the devices, for instance while the X-ray was off for instance.

Pre-stored features extracted for the last frame in the previous sequence may be retrieved to perform the clustering for the instant first frame $F_1$, and similar for all other frames in the sequence, using the features from the previous frame in the instant sequence. Notably, the anatomical features can now be disregarded in branch "A" for processing at step S4020A and the clustering may be done solely based on shape similarity and/or in-image position. In particular, the weight w of the anatomical location feature may be set to "zero" so as to nullify its influence on the clustering when optimizing cost function (1).

If, however, it is determined that an imaging geometry change has occurred, the clustering algorithm is modified and process flow proceeds according to branch "B".

In particular, the cost function $f$ may be modified so as to now take into account the anatomical position for the footprint(s) in the given frame and to use this in the identification operation S420 to associate the footprints with the respective device. In other words, in step S42020B the anatomical position is determined for a given footprint and in step S42030B the identification is then carried out by taking into account the anatomical positions of the footprints in the given current frame and the next frame $F_2$. When processing in branch "B", it is the shape and/or the in-image location that is now disabled by setting one or both weights to zero as the shape and in-image location are now no longer expected to be relevant. Once the initial clustering in relation to frames $F_1, F_2$ has been determined, when processing the follow up frames in branch "B", it is now again the anatomical features that can be "re-disabled" and the remaining clustering can again proceed as in branch "A" based only on shape similarity and/or in-image position, until the next geometry change occurs in which case flow returns to step S42010.

In branch "B", the determination of the change in anatomical position may be based on receiving an indicator signal received from the imaging apparatus that is indicative of the imaging geometry change. As an alternative, the indicator signal may not only indicate the imaging geometry change that has occurred, but the signal may include enriched information that specifies how the imaging geometry change has changed. For example, the indicator signal may specify any one or more or all of: angulation, rotation angle, translation, table height. Alternatively, this event could be detected from the images directly, for instance by machine learning, with a machine learning model trained based on the following input, output pairs: Input: two images. Output: Boolean indication where the two images are in the same imaging geometry or not.

If the shape geometry of some or each device is known in 3D, for instance are available as pre-stored models, the new shapes as per the new imaging geometry may be pre-computed from the old ones by a forward projection along a direction as specified by the indicator signal. The cost function as such may then be changed by updating the shape information. In similar manner, the in-image position may be updated. Preferably, patient motion, such as heart-beat or breathing induced, is taken into account by motion compensation techniques.

Turning now to the branch "C" where the current frame is not the first frame of a given sequence in step S42020C, the identification of footprints with their respective device, that is the clustering, may now proceed by disregarding the anatomic position p(TF) and proceed purely based on features shape similarity and/or in-image location f(TF) as retrieved from memory MEM.

If at step S42030C it is determined that the current frame is the last frame in the given sequence, the anatomical position is still determined, associated with the respective footprint(s), and committed to memory MEM. The anatomical position(s) for footprints in the last frame may then be used for clustering in a follow up sequence should an imaging geometry occur. Clustering may then proceed for the new sequence as per branch A or B as described above.

For each frame so processed with the respective devices identified therein the tagging can be applied at step S430 as described above in a consistent and persistent manner to form the tagged sequence $F_i'$.

Within a given sequence or if no imaging geometry occurred between two sequences, the anatomical location feature is not needed and it is preferably only the "internal" features, that is shape, and/or in-image position, that is used for the clustering. The anatomical feature is invariant to imaging geometry changes. In this manner, by using imaging geometry change invariant information when needed, the proposed dynamic clustering scheme can be robustly adapted to ensure a consistent and persistent tagging across a plurality of possibly different sequences as acquired. The features for the clustering are used dynamically, with the anatomical location feature only included when required, in particular for the first frame in a new sequence after imaging geometry change, with the anatomical location feature being preferably ignored otherwise to simplify the optimization.

The above mentioned further robustness against new devices being added and or device(s) being removed is achieved by attaching a cost G( ) to the number of clusters. This can be achieved as described above by adding an implicit or explicit cost term for the number of clusters to be considered. The clustering algorithm acts conservatively in relation to opening up a new cluster or reducing the number of clusters. Furthermore, previously identified devices that are removed and later reintroduced in the FoV, can be robustly re-identified by using the shape features in conjunction with in-image location features for the clustering problems (1), (2). It is assumed herein in embodiments, that removal or reintroduction of a given device is due to an imaging geometry change so that a device is no longer in a new Fov due to imaging geometry change or that an earlier device reenters the new Fov due to the imaging geometry change. It is assumed herein for best performance of the proposed method and system that the affected devices that reenter the Fov after imaging geometry change have not been moved. This assumption then allows for a more robust re-identifying of the device, that is, reassignment to the correct cluster and consistent retagging. This assumption is also consistent with clinical practice where catheters, guide wires or other tools are not moved when put of FoV.

In order to resolve this ambiguity in relation to (re-) appearance/disappearance of medical devices, the processing may be based on indicator signals as provided by the user for example to so direct the identification step to change the number of clusters. However, a fully automatic embodiment is also envisaged, where, as mentioned above, the cost function evolution is observed. A rise in cost may be used as an indication that a new device appeared, or a known device reappeared, or a device was removed. As explained above, the "removal" of the device is assumed in embodiments to have occurred due to change in imaging geometry with consequential change of the FoV. If a given footprint cannot be matched at a reasonable cost, it must belong to a device that was not in the earlier frame of the considered pair of frames. A set or user-definable cost function thresholding may be used to determine whether to change the number of clusters. Conversely, if an existing cluster does not match any segmentation at a reasonable cost in terms of similarity, the corresponding device must have exited the image.

Another complication may arise in that in some imaging geometries, specifically along some projection directions, footprints can fully or at least partially overlap. It is likely that the frames with overlapping footprints may not be fully disambiguated.

However, once one of the devices is advanced so that the two no longer overlap, we can expect to re-identify the devices by comparing their shape post-overlap with their shape pre-overlap, possibly considering further geometrical features such as length, curvature, etc. If the situation cannot be disambiguated in this manner, one possible strategy is to assume that only one of both guide wires has been moved during the overlap period, so that the respective tags associated to the static and moving device, respectively, should be preserved as assigned before the overlap occurred.

If the situation in relation to overlap cannot be fully disambiguated, the proposed system may issue an alert warning by indicating an uncertainty in relation to the tagging. The relevant overlap portion may be highlighted by color-coding or line-type coding. In addition, a question mark or other indicia may be appended to the relevant tag. Optionally, the system IPS may invite the user to re-establish a reliable tagging through a suitable interface. For instance, a voice command handler may be used to receive a command such as "label correct/switch labels 1 and 3" to request a re-tagging.

Figure 6:
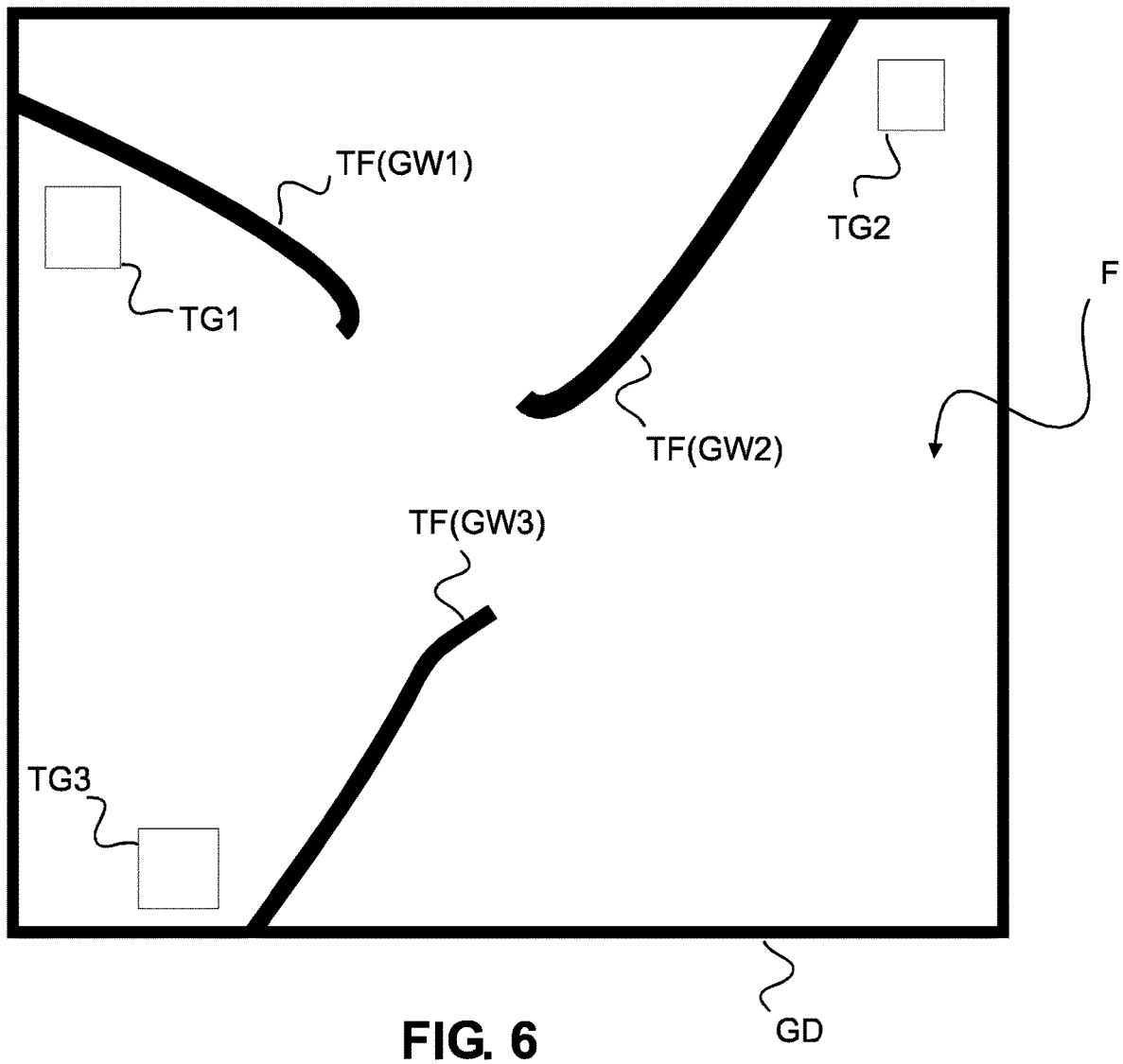
FIG. 6 is a schematic representation of a graphics display according to one embodiment.

FIG. 6 is a schematic representation of a graphics display GD envisaged herein according to one embodiment. The graphics display GD is displayed on a device DD. The GD includes three transmission footprints TF(GW1)-TF(GW3), each having its own distinct tag TG1-TG3, respectively. FIG. 6 illustrates explicit tagging. Some or all tags may include alphanumeric strings, e.g. text, to provide further information. The information may encode, by ordinal numbers, the order in which the respective devices GW1-GW3 were introduced into the FoV. That is, the tagging is chronological and follows the order in which the various device appear and are identified by the identifier ID. The chronological order may be coded by tags including incremented numbers and/or by color or otherwise.

Operation of the proposed system and method may be further illustrated by the following use case: suppose there are two (or more) devices recorded in a current frame, each having been tagged, say by color coding of their footprints, one in red and one in blue. Assume that the device with the blue footprint is removed, whilst the device for the red footprint remains for the follow up frames. Then, at one point in time during the imaging, a new device, not previously seen, is introduced. This new device may then be tagged in a color other than blue and red, as these tags are already taken up by the two earlier mentioned devices. The footprint of the new device may be for example tagged in green. The red and blue tagging will only show up if either one or both of the two initial devices are present. As envisaged herein in embodiments, once tagged, the device retains its unique tag which persists preferably throughout the imaging. Its tagging scheme may not be used by other devices.

One or more features disclosed herein may be configured or implemented as/with circuitry encoded within a computer-readable medium, and/or combinations thereof. Circuitry may include discrete and/or integrated circuitry, application specific integrated circuitry (ASIC), a system-on-a-chip (SOC), and combinations thereof, a machine, a computer system, a processor and memory, a computer program.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for supporting image-based navigation, the system comprising:
   an input interface for reviving one or more input images acquired by an X-ray imager whilst two or more medical devices are present, at the a same time or at different one or more times, in a field of view of the X-ray imager;
   an image identifier configured to identify the two or more medical devices based on image information in the one or more input images, the image identifier thereby capable of distinguishing between the two or more medical devices;
   a tagger, configured to associate respective tags with each of at least two of the two or more medical devices so identified; and
   a graphics display generator configured to display on a display device the one or more input images in a video feed, with the tags included;
   wherein at least one further input image is received at the input interface, and the graphics display generator is configured to display on the display device, only when the image identifier re-identifies in the at least one further input image at least one of the two or more medical devices, the at least one further input image as part of the video feed, thereby including a same tag as earlier associated by the tagger with the said at least one of the two or more medical devices.

2. The system of claim 1, wherein the image identifier includes a detector module configured to detect transmission footprints in the one or more input images caused by a presence of the two or more medical devices in the field of view.

3. The system of claim 2, wherein the tagger is configured to implement a clustering algorithm to process the detected transmission footprints into clusters, each cluster corresponding to one of the two or more medical devices.

4. The system of claim 2, wherein the tagger is capable of changing a number of clusters in dependence on whether a new medical device is present or at least one of the two or more medical devices is removed.

5. The system of claim 2, wherein an association operation by the tagger is based on one or more features, the one or more features including one or more of a combination of: a respective shape of the detected transmission footprints, a current respective image position of the detected transmission footprints, and a current anatomical location of a respective medical device.

6. The system of claim 1, wherein at least two of the two or more input images or of the at least one further input image is acquired at different imaging geometries.

7. The system of claim 5, wherein the tagger is configured to selectively adjust an influence of one or more of the one or more features on the association operation, in dependence on a change of the X-ray imager's imaging geometry.

8. The system of claim 1, wherein the one or more input images are one or more projection images.

9. The system of claim 1, wherein at least one of the two or more medical devices is a guidewire.

10. The system of claim 1, further comprising at least one of the X-ray imager or the display device.

11. A method for supporting image based navigation, the method comprising:
receiving one or more input images acquired by an X-ray imager whilst two or more medical devices are present, at the a same time or at different one or more times, in a field of view of the X-ray imager;
identifying the two or more medical devices based on image information in the one or more input images, the image identifier thereby capable of distinguishing between the two or more medical devices;
associating a respective, unique, tag with each of at least two of the two or more medical devices so identified; and
displaying on a display device the one or more input images in a video feed, with the tag associated with each of the at least two of the two or more medical devices included; further comprising:
receiving at least one further input image and,
displaying on the display device the at least one further input image as part of the video feed only when in the at least one further input image at least one of the two or more medical devices is re-identified, thereby including a same tag as earlier associated with the said at least one of the two or more medical devices.

12. A computer program element, which, when being executed by at least one processing unit, causes the at least one processing unit to perform the method as per claim 11.

13. A non-transitory computer readable medium having stored thereon the computer program element of claim 12.

* * * * *